(12) United States Patent
Kipman

(10) Patent No.: US 6,525,810 B1
(45) Date of Patent: Feb. 25, 2003

(54) NON-CONTACT VISION BASED INSPECTION SYSTEM FOR FLAT SPECULAR PARTS

(75) Inventor: Yair Kipman, Waban, MA (US)

(73) Assignee: imageXpert, Inc., Nashua, NH (US)

( * ) Notice: Subject to any disclaimer, the term of this patent is extended or adjusted under 35 U.S.C. 154(b) by 0 days.

(21) Appl. No.: 09/438,178

(22) Filed: Nov. 11, 1999

(51) Int. Cl.$^7$ ............................................. G01N 21/88
(52) U.S. Cl. ................................................. 356/237.1
(58) Field of Search ..................................... 356/237.1

(56) References Cited

U.S. PATENT DOCUMENTS 4,772,125 A * 9/1988 Yoshimura et al. ...... 356/234.7
4,875,778 A * 10/1989 Luebbe et al. ........... 356/237.1
5,532,815 A * 7/1996 Kipman et al. ......... 356/139.03

* cited by examiner

Primary Examiner—Richard A. Rosenberger
(74) Attorney, Agent, or Firm—Iandiorio & Teska; Kirk Teska; R. Stephen Rosenholm

(57) ABSTRACT

A non-contact vision based inspection system and method for flat specular parts in which an imaging camera defining an image plane is aimed at a part to be inspected for taking a single image of the part. A staging apparatus is used to move the part relative to the camera until the single image of the part is obtained. The image plane is fixed to remain parallel to the object plane defined by the part as the part moves relative to the imaging camera.

16 Claims, 6 Drawing Sheets

NON-CONTACT VISION BASED INSPECTION SYSTEM FOR FLAT SPECULAR PARTS

FIELD OF INVENTION

This invention relates to a non-contact vision based inspection system for flat specular parts such as ink jet printer nozzle plates.

BACKGROUND OF THE INVENTION

Ink jet nozzle plate production includes the step of inspecting each nozzle for morphological defects such as nicks, cuts, or blockages. Defective nozzles result in compromised print quality. Once the nozzle plates are integrated into the print head assembly, print testing can be used to verify print head performance but inspection at this stage in the production process is often imprecise and requires, upon the detection of an improperly manufactured nozzle plate, the time consuming and expensive rework required to replace the defective nozzle plate.

Traditionally, the nozzle plates were not inspected directly and only tested through print testing after integration into print head assemblies. In other cases, a human operator would view the nozzle plate under a microscope and decide whether the nozzle plate passed or failed based on subjective, visual criteria. More recently, inspection by human observers has been augmented by the use of automated inspection methods. Still, these methods rely heavily on human observers for final go/no-go determination and there is an inflated false failure rate associated with these current automated inspection methods and systems. There is currently no high speed automated process which accurately inspects ink jet nozzle plates for morphological defects. One current inspection system includes the use of a 2-D CCD array camera as the primary imaging input device. Ink jet nozzle plates are small, generally long and skinny and have over a thousand very small, e.g. 301 $\mu$m nozzle orifices and thus require high magnification for adequate assessment. Using a 2-D CCD array camera poses a variety of challenges. Since the captured image size is limited by the size of the array, the camera needs to be stepped across the part surface in order to make a complete assessment of the surface characteristics. Even using this system, challenges such as illumination, depth of focus, part orientation, and image capture speed have resulted in falsely inflated part rejection rates. The use of the 2-D CCD array camera based system involves a very time consuming inspection process riddled with potential sources for error from focusing, illumination, and placement. The 2-D CCD array camera must be focused at each step since the depth of focus is prohibitively small for high magnification, large field of view circumstances. The illumination angle is also critical since nozzle plate materials are most often highly specular and difficult to image. Also, heat is an issue which may cause damage to a nozzle plate due to mismatched coefficients of thermal expansion of materials used in manufacturing ink jet heads. Accordingly, illumination sources which are heat intensive can not be used. Also, illumination uniformity is a significant challenge for use with 2-D cameras as illumination levels often fall off towards the perimeter of the camera causing undesired perturbations in the resulting data.

Assuming that both illumination and focus are controlled, the composite image in the prior 2-D CCD camera based system is stitched together from the separate images collected at each focusing step and reconstructed in a single buffer in order to be analyzed. This process results in another potential error along the stitching boundaries where adjacent fields are abutted. Any variations in the placement of the part or the camera results in incorrect, partial, or repeated data along the boundary lines which makes measurements very difficult. In order to eliminate the stitching operations, each image may be inspected separately resulting in a severe increase in the inspection time and cost. The use of a 2-D CCD array camera is also quite wasteful in terms of processing time as only approximately 5% of the useable elements are actually used for the nozzle array inspection. The rest of the array elements image unimportant peripheral areas of the nozzle plate away from the nozzle orifices.

BRIEF SUMMARY OF THE INVENTION

It is therefore an object of this invention to provide a non-contact vision based inspection system for flat specular parts.

It is a further object of this invention to provide such a system which more accurately inspects flat specular parts such as ink jet print head nozzle plates automatically and very quickly.

It is a further object of this invention to provide such a system which produces a single image of an entire ink jet print head nozzle plate thus eliminating the problems associated with stitching together individual images to form a composite image.

It is a further object of this invention to provide such a system which does not require refocusing of the imaging camera as it scans the part under inspection.

The invention results from the realization that the fine details (e.g. the 30 $\mu$m nozzle orifices) of flat specular parts (e.g. nozzle plates) can be more accurately imaged and inspected not by taking successive images of each portion of the part, refocusing the imaging camera prior to capturing each image, and then stitching together the successive images to form a composite image of the whole part but instead by ensuring that before any image is taken the image plane defined by the imaging camera is rendered parallel to the object plane defined by the part and then using a linescan camera to scan the length of the part to capture a high quality single image of the whole part without the need to refocus the camera during the scan.

This invention features a non-contact vision based inspection system for flat specular parts, the system comprising an imaging camera defining an image plane and aimed at a part to be inspected for taking a single image of the part; a staging apparatus for moving the part relative to the camera until the single image of the part is obtained; and means for ensuring that the image plane remains parallel to the object plane defined by the part as the part moves relative to the imaging camera.

The imaging camera is preferably a linescan camera. The part is typically located on a translatable table and the camera is fixed in place with respect to the translation direction of the table.

The means for ensuring that the image plane and the object plane are parallel may include a goniometer between the part and the translation table for rotating the orientation of the part relative to the image plane. An optical source and a detector measure the distance between two points on the part and the image plane. The goniometer is located on the staging apparatus. A controller is programmed to be responsive to the optical source, the detector, and the goniometer for adjusting the orientation of the part until the object plane is parallel to the image plane.

Further included may be means for adjusting the distance between the image plane relative to the object plane for focusing the imaging camera. A magazine is typically disposed on the staging apparatus for holding a plurality of long narrow parts to be inspected in sequence. The system is particularly suited to the inspection of ink jet printer nozzle plates.

This invention also features a non-contact vision based inspection system for flat specular parts including ink jet nozzle plates. A linescan camera defines an imaging plane and is aimed at a part to be inspected for taking a single image of the part. A staging apparatus is provided for moving the part relative to the camera until the single image of the part is obtained. An optical source and a detector measure the distance between two points on the part and the image plane. A goniometer is disposed between the part and the staging apparatus. A controller is programmed to activate the goniometer in response to the optical source and the detector until the object plane defined by the part is parallel to the image plane.

A CCD array camera may be used and aimed at the part for locating a terminal end of the part. The controller is further programmed to activate the staging apparatus to move a terminal end of the part proximate the optical source, to activate the optical source and then again to activate the staging apparatus to move an opposite terminal end of the part proximate the optical source, and to again activate the optical source.

The method of inspecting flat specular parts in accordance with this invention includes placing a part in a spaced relationship with respect to an imaging camera, the part defining an object plane, the imaging camera defining an image plane; adjusting one of the object plane and the image plane until they are parallel to each other; and moving the imaging camera relative to the part until a single image of the part is recorded.

The method also typically comprises: locating an edge of the part; determining the location of the opposite edge of the part; calculating height difference between two edges of the part; adjusting the orientation of the part until the height difference between the two edges of the part is below a predetermined threshold; focusing a linescan camera at one edge of the part; scanning the part with the linescan camera until the full part is imaged with the single image; and using the image of the part as input to an inspection algorithm to inspect the part for defects.

Another feature of this invention is an imaging head for a non-contact vision based inspection system, the imaging head comprising an optical housing including a mount for a linescan camera and a 2D CCD array camera; a light source; means for directing light from the light source to a part to be inspected; means for directing light reflected from the part simultaneously to both the linescan camera and the 2D CCD camera; and a distance measuring device attached to the housing for measuring the orientation of image plane defined by the linescan camera relative to the object plane defined by the part. The means for directing light reflected from the part typically includes a beam splitter in the optical housing positioned to direct light to both the linescan CCD camera and 2D CCD array camera.

BRIEF DESCRIPTION OF THE DRAWINGS

Other objects, features and advantages will occur to those skilled in the art from the following description of a preferred embodiment and the accompanying drawings, in which.

PREFERRED EMBODIMENT

Figure 1:
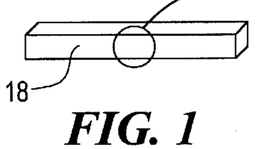
FIG. 1 is a schematic view of a nozzle plate to be inspected in accordance with the subject invention.
Figure 2:
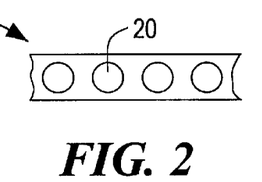
FIG. 2 is a top view of a portion of the nozzle plate of FIG. 1 showing the nozzle orifices present in the nozzle plate.

A typical ½ inch long ink jet nozzle plate 18, FIG. 1 includes upwards of 1000, 30 $\mu$m ink jet nozzle orifices 20, FIG. 2 which must be inspected prior to assembly of the nozzle plate into an ink jet printer. Because of the small size of each nozzle orifice, it is difficult to automatically inspect the nozzles for blockages and other manufacturing defects.

Figure 3:
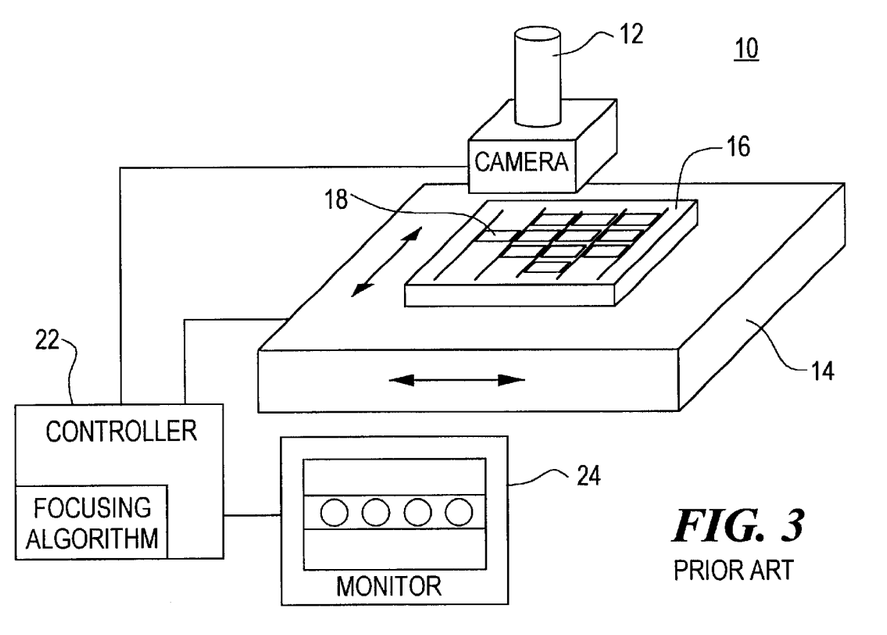
FIG. 3 is a schematic view of a prior art nozzle plate inspection system.

Prior art ink jet nozzle inspection system 10, FIG. 3 included 2-D CCD array camera 12 and XY stage or translation table 14 upon which was mounted magazine 16 which held a number of ink jet nozzle plates 18.

Figure 4:
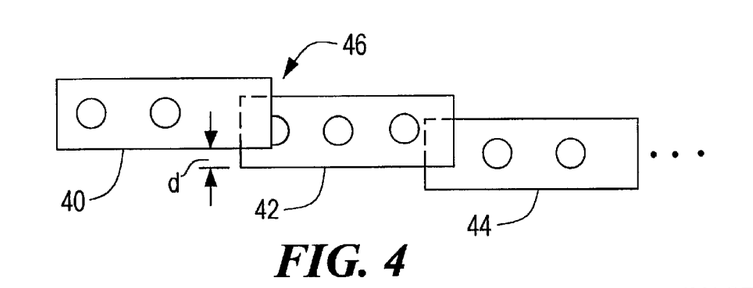
FIG. 4 is a top view of a portion of a composite image of a nozzle plate formed by stitching together a number of successive images.

Controller 22 which includes a focusing algorithm operating on a microprocessor (not shown) controls stage 14 to bring nozzle 18 underneath camera 12. Controller 22 also controls the focusing of camera 12 and brings camera 12 into focus on, for example, the far left side of plate 18. An image is then taken of one portion of plate 18. Stage 14 is then moved slightly, the camera refocused, and another image taken of another portion of plate 18. This process is repeated numerous times and the individual images 40, 42, 44, etc., FIG. 4 are stitched together to form a composite image of plate 18 which can be viewed on monitor 24, FIG. 3, and/or provided as input to computer software operating on controller 22 which provides for the inspection of individual nozzles 20, FIG. 2 of nozzle plate 18. Alternatively, each individual image is inspected.

The primary problems associated with such a prior art system include the stitched together images and the cumbersome and time consuming need to refocus camera 12 between successive images which result in a costly inspection process.

When the images are stitched together as shown in FIG. 4, it is possible to miss all or portions of individual nozzles as shown at 46. Also, the possible misalignment d between successive images make it difficult to make sense of or to measure certain features of the resulting composite image formed by stitching together the individual images.

Refocusing the camera between successive images is required because the nozzle plates do not lay completely flat in magazine 16, FIG. 3 and/or because of the inherent unflatness of magazine 16 with respect to stage 14. So, the object plane 15, FIG. 5, defined by the nozzle plate is not parallel to the image plane 52 defined by the optical components of camera 12, FIG. 1.

Figure 5:
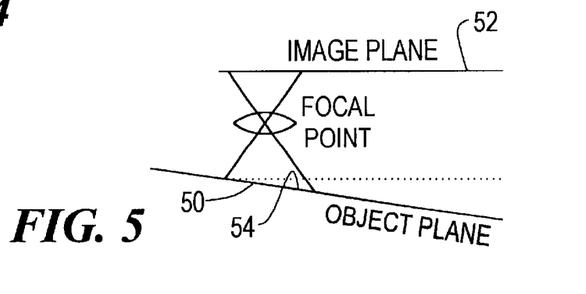
FIG. 5 is a view showing the non-parallel relationship between the image plane and the object plane associated with the prior art inspection system shown in FIG. 3.

Besides the problems associated with focusing camera 12 between successive images, the non-parallel relationship between image plane 52, FIG. 5 and object plane 50 results in an unfocused images at area 54 and a loss of light since the nozzle plate is skewed as shown.

Figure 6:
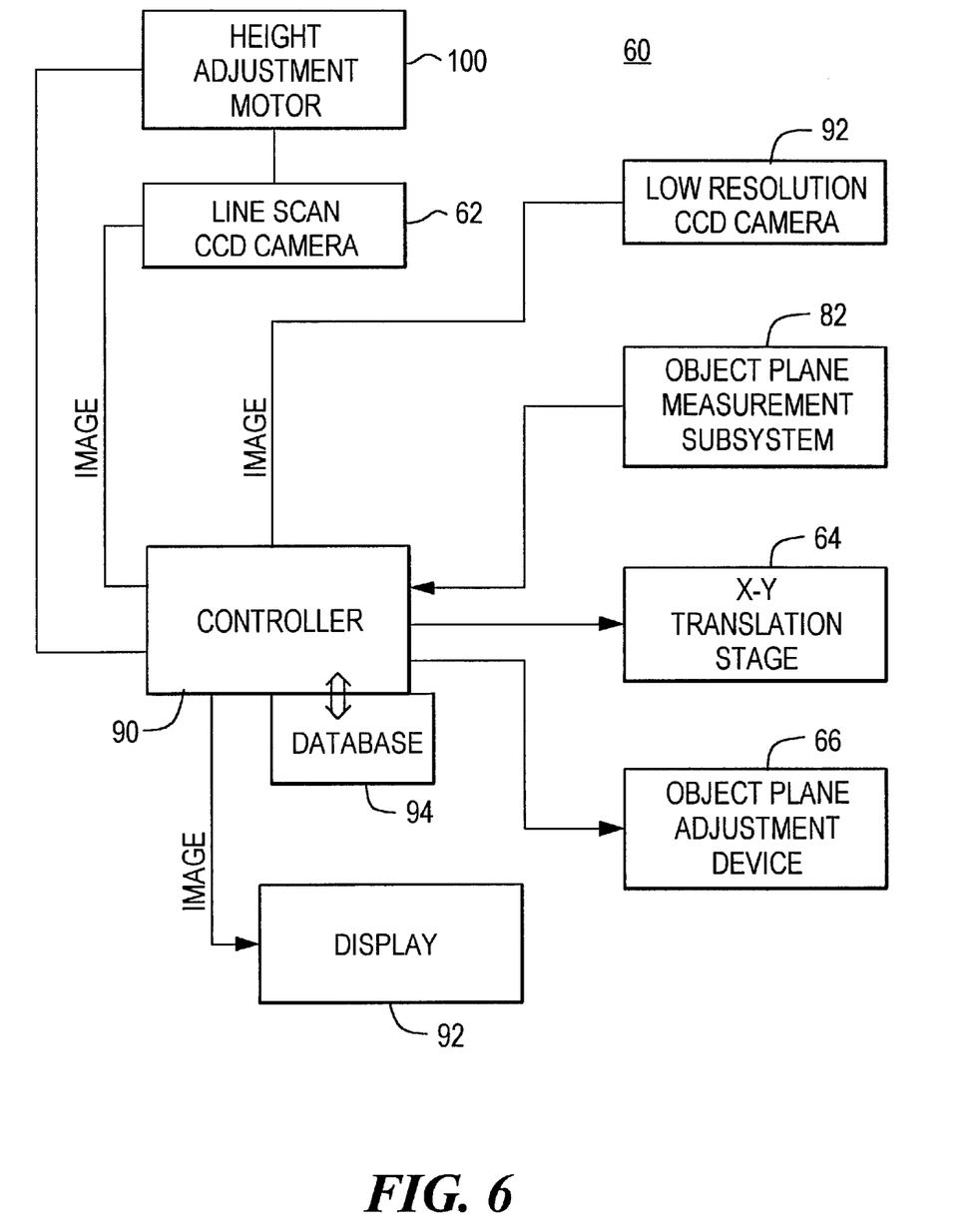
FIG. 6 is a block diagram of the non-contact vision based inspection system for flat specular parts in accordance with the subject invention.
Figure 7:
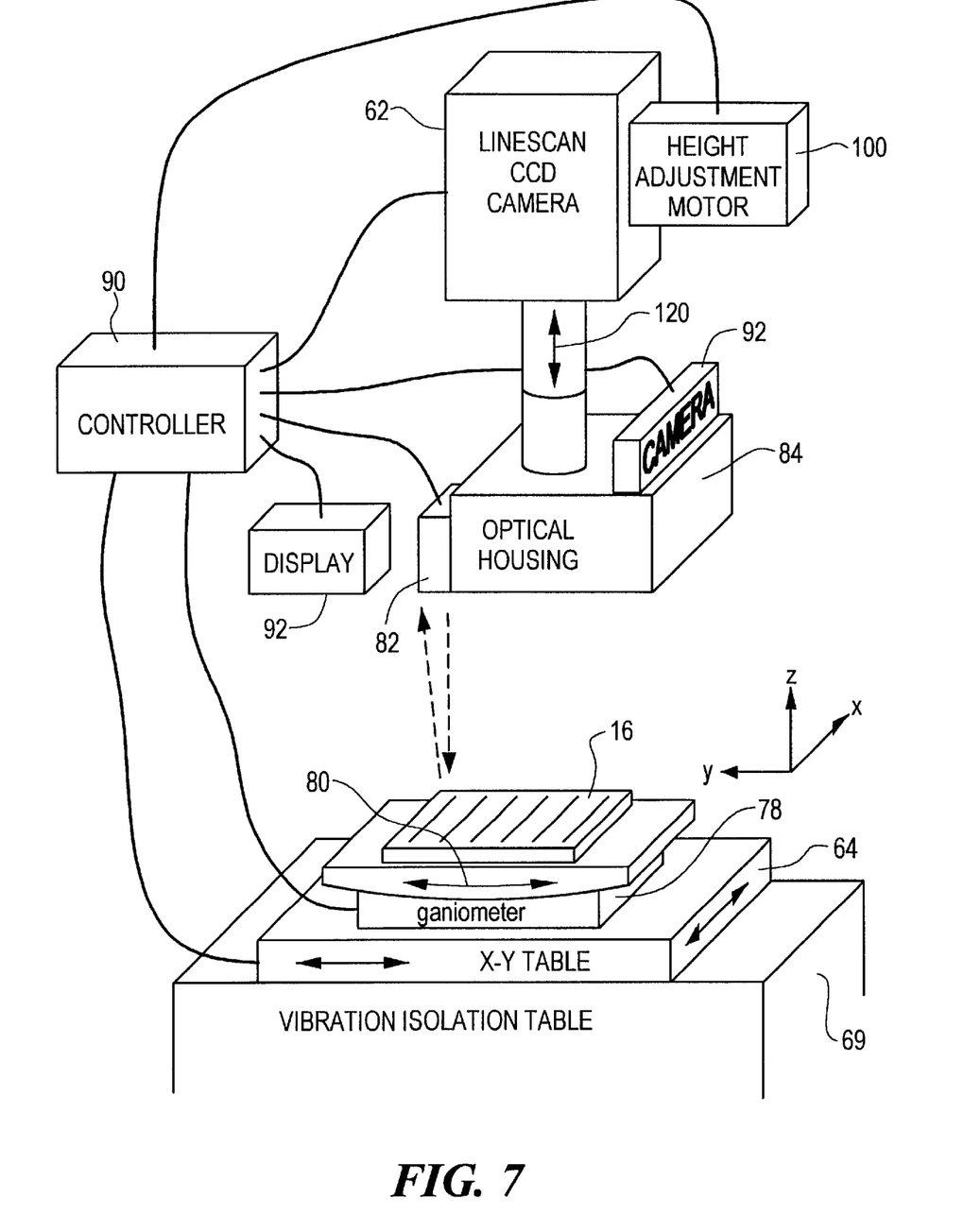
FIG. 7 is a schematic view showing the primary components associated with the non-contact vision based inspection system of this invention.

Non-contact vision based inspection system 60, FIGS. 6–7, of this invention, in contrast, ensures a more accurate and higher quality image and inspection and, indeed, a complete instead of a composite image of a whole part by ensuring that at all times any imaging occurs the image plane defined by the imaging camera is rendered parallel to the object plane defined by the part and by using a linescan camera to scan the length of the part to capture a higher quality single image of the whole part without the need to refocus the camera during scanning.

System 60 includes a fixed in place linescan CCD imaging camera 62 defining an image plane and aimed at a part to be inspected for taking a single image of the part instead of a composite image made up of a number of stitched together successive images of portions of the part.

A staging apparatus, preferably XY translation table 64, moves the part relative to camera 62 until the single image of the part is obtained.

There is also some means for ensuring that the image plane remains parallel to the object plane defined by the part as the part moves relative to the imaging camera. In the preferred embodiment, such means includes an object plane adjustment device 66 such as goniometer 78, FIG. 7 on XY table 64 which is positioned on vibration isolation table 69. Nozzle plate magazine 16 lies on goniometer 78. When goniometer 78 is rotated in the direction shown by arrow 80, the orientation of each plate is adjusted until the object plane defined by the part is rendered parallel to the image plane defined by the camera.

In order to detect whether the object plane is parallel to the image plane, object plane measurement subsystem 82, FIGS. 6 and 7 is employed which preferably includes an optical source such as a laser and a detector attached to optical housing 84 for measuring the distance between two points on the part and the image plane (or some other reference plane parallel to the image plane). See U.S. Pat. No. 5,532,815 which is incorporated here in this reference. Other laser based laser beam triangulation subsystems may be used.

Controller 90, FIGS. 6 and 7 (which could be a single computer or any number of computers, microprocessors, numerical control devices, and the like) receives a signal from low resolution 2-D CCD camera 92 and in conjunction with imaging software resident in controller 90 provides a signal to XY table 64 to move it in the direction of the X and Y axes until one edge of the nozzle plate under inspection is located beneath the optical source of object plane measurement subsystem 82. A laser is then activated and the distance between the part and the image plane calculated. The length of the part is known and thus controller 90 sends a signal to XY table 64 to move it until the opposite edge of the plate is now located beneath subsystem 82. Again, the distance between the part and the image plane is calculated.

Controller 90 then sends the appropriate signal to goniometer 78 to adjust the orientation of the part until the object plane is parallel to the image plane. The distance between one end of the part and the other end of the part relative to the image plane will now be the same or the difference between these two distances, $d_1$ and $d_2$, FIG. 8, below some predetermined threshold. The part is now guaranteed to be in focus during the imaging operation since the image plane and the object plane are parallel or nearly parallel.

Controller 90 also operates linescan camera height adjustment motor 100, FIGS. 6 and 7 to adjust the distance between the image plane relative to the object plane for focusing imaging camera 62 prior to imaging. This process also ensures that the magnification level is constant from part to part.

Controller 90 next causes XY table 64 to position one edge of the now aligned part to be under linescan camera 62 and then activates linescan camera 62 to begin imaging along the length of the part slowly moving (e.g. 1 mm/sec) X-Y table 64 until a single complete image is rendered whereupon the process described above is repeated for each part disposed in magazine 16.

The imaging data may be displayed on monitor or display 92, captured in database 94 (FIG. 6) and/or provided as input to inspection software operating on controller 90, for example, ImageXpert™ imaging quality measurement software available from KDY, Inc., Nashua, N.H.

Figure 9:
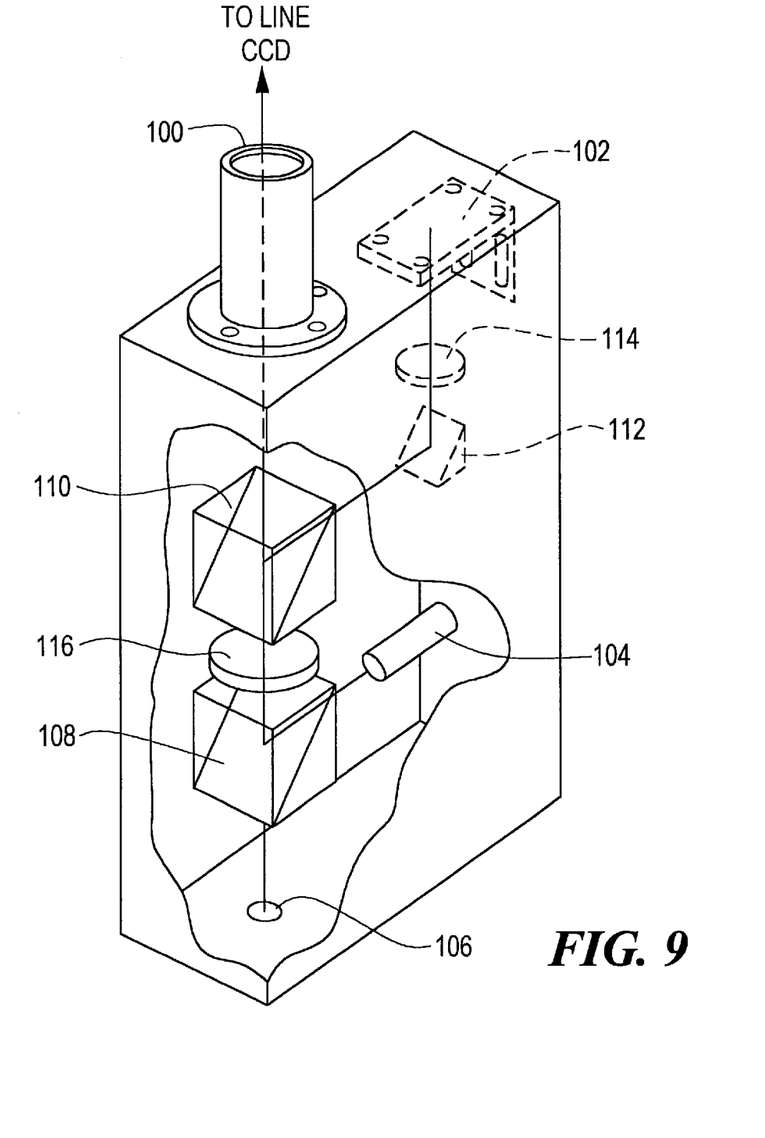
FIG. 9 is a schematic view showing the primary components associated with the optical housing of the system shown in FIG. 7.
Figure 10:
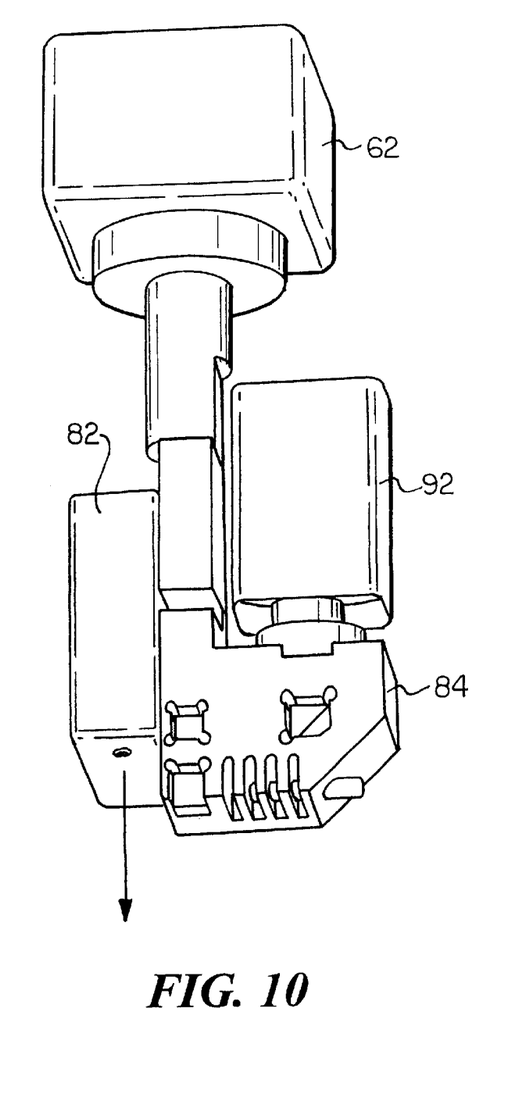
FIG. 10 is a front elevational view showing the assembly of the primary imaging components of the system of this invention.

The optical components of optical housing 84, FIG. 7 and 10 are shown in FIG. 9. In general, housing 84 provides for robustness and stability of the imaging components of the system. Orifice 100 receives a Dalsa CCD 1024 Linescan camera (camera 62, FIG. 7) with a field of view of 120 microns. A 640×480 CCD camera (92, FIG. 7) with a field of view of 3–4 mm is mounted to mount 102. Light source 104 available from Welch Allan, Inc. provides an illumination beam to the part through orifice 106 via beam splitter 108 and to both the linescan camera and the CCD array camera via beam splitter 110 and right angle prism 112 and lenses 114 and 116. The distance between lenses 114 and the area CCD camera is fixed at 57.93 mm. Lens 114 is a 01LA0117 MG precision optimized lens available from Achromat with an EFL of 90.018, a diameter of 19.0 mm and a thickness of 5 mm. 10×10 mm right angle prism 112 is 5 mm from lens 114 and 10 mm from beam splitter 110. Lens 116 is a 01LA005 MG precision laser grade lens available from Melles Griot (EFL=20 mm, diameter=10 mm, thickness=5.89 mm) positioned 1 mm from beam splitter 110 and 1 mm from beam splitter 108 which is 11.7 mm from the object plane.

In the preferred embodiment, optical head 84, FIG. 10 is fixed in place over magazine 16, FIG. 7 which rotates by virtue of goniometer 78 about an axis (e.g. the X axis) perpendicular to longitudinal axis (e.g. the Y axis) of the part under inspection. Controller 90 provides signals to XY table 64 to move magazine in the direction of both of these axis. Height adjustment motor 100 moves linescan CCD camera 62 in a direction perpendicular to both of these axis (e.g. the Z axis) as shown by arrow 120 to adjust location of the image plane with respect to the object plane for optimum magnification and focusing.

Figure 8:
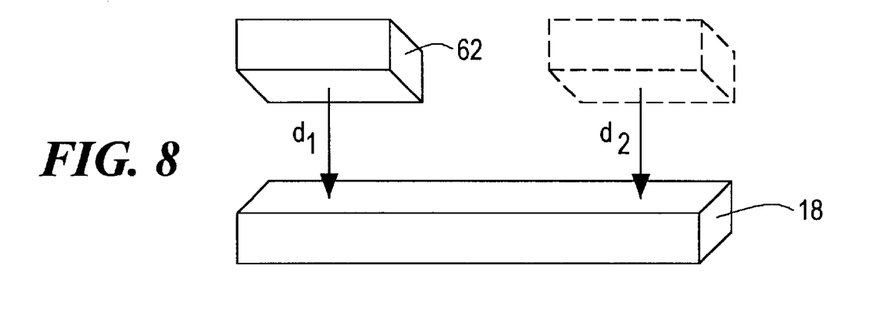
FIG. 8 is a schematic view showing the parallel relationship between the image plane and the object plane in accordance with one aspect of the non-contact vision based inspection system of this invention.
Figure 11:
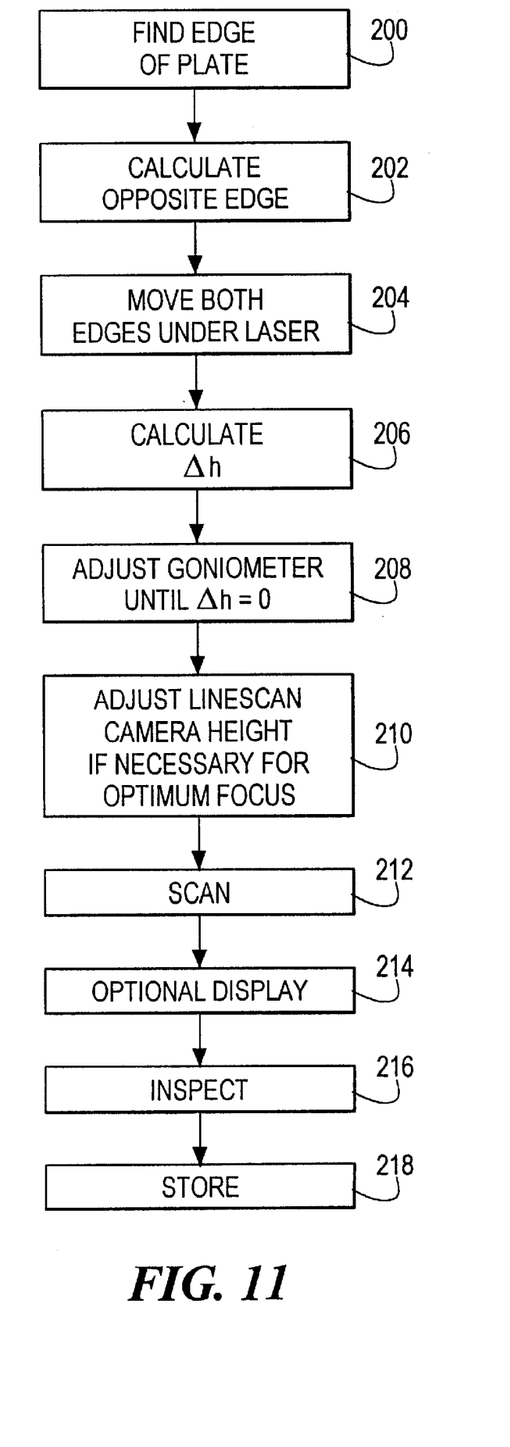
FIG. 11 is a block diagram depicting the primary steps associated with inspecting flat specular parts in accordance with this invention.

Thus, controller 90, FIGS. 6 and 7 is programmed to first find the coordinates of one edge of a nozzle plate, step 200, FIG. 11 by interfacing with the image obtained by low resolution camera 92 and XY table 64. The location of the opposite edge is evaluated based on these coordinates and the known length of the part, step 202, FIG. 11. The next step is to determine whether the image plane is parallel to the object plane. Controller 90, FIGS. 6 and 7 determines the orientation of the object by moving both edges of the part under the laser beam output of the object plane and measurement subsystem 82, FIGS. 6–7, step 204, FIG. 11. Subsystem 82 determines $d_1$ and $d_2$, FIG. 8 and calculates $\Delta h$, the difference between $d_1$ and $d_2$, step 206, FIG. 11. Controller 90 next sends a signal, if $\Delta h$ is not zero or below some predetermined threshold, to goniometer 78, FIG. 7 to activate it until the threshold $\Delta h$ difference between $d_1$ and $d_2$, FIG. 8, is achieved, step 208, FIG. 11. Controller 90, FIGS. 6–7 then sends a signal to height adjustment motor 100 to adjust the height of linescan camera 62 if necessary for an optimum focus, step 210, FIG. 11. The entire part is then imaged by moving XY table in the direction of the longitudinal axis of the part thus scanning the part, step 212, FIG. 11. This complete, single image may be displayed, step 214, for manual inspection but controller 90 preferably provides the digital data representing the image to inspection software, step 216 for analysis and/or to storage for later review, step 218.

Figure 12:
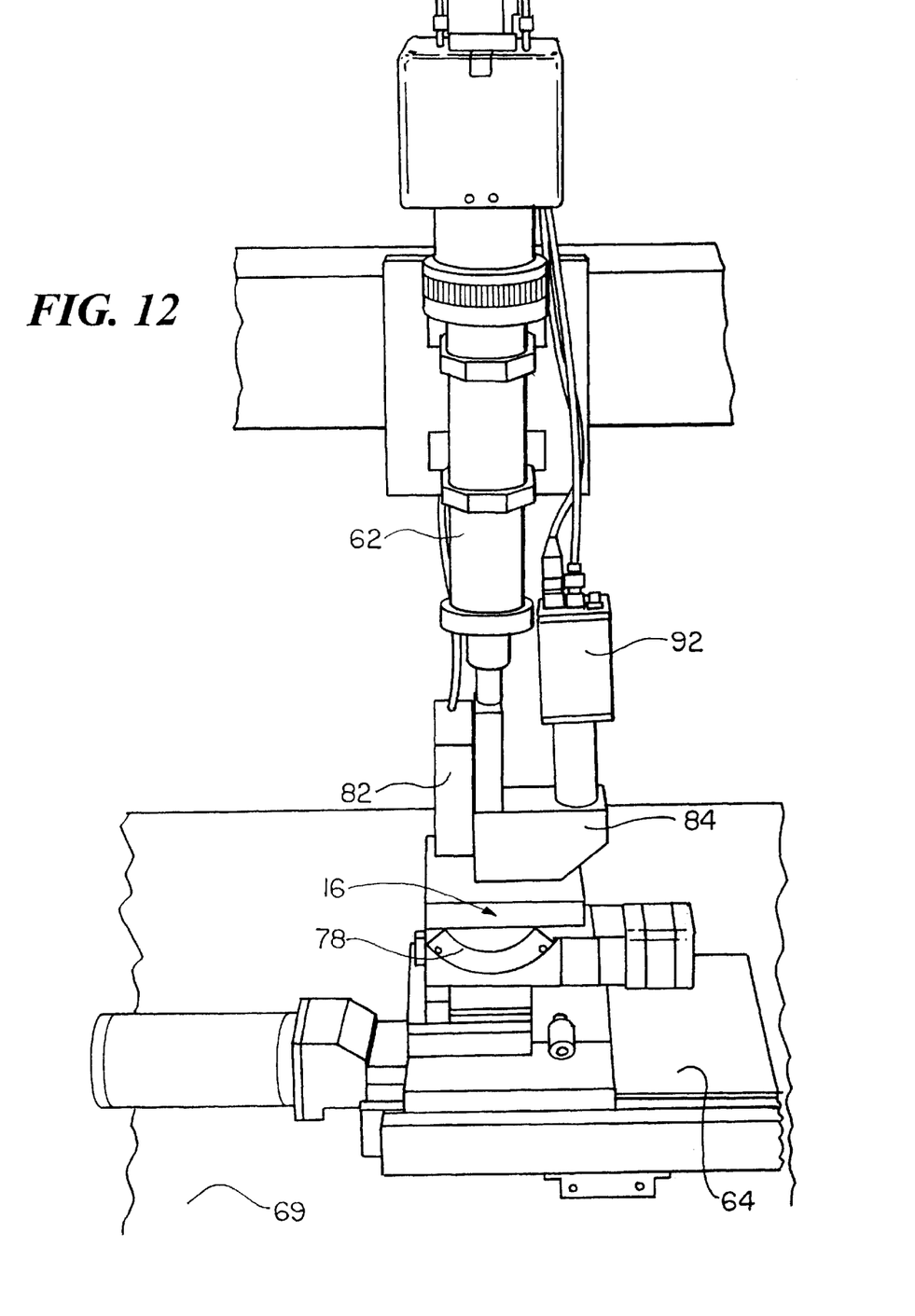
FIG. 12 is schematic front view of the primary components associated with the system of this invention.

FIG. 12 shows the assembling for carrying out these steps including cameras 62 and 92, subsystem 82, optical head 84, magazine 16, goniometer 78, XY table 64, and vibration isolation table 69.

Although the disclosure above is primarily rated to the inspection of ink jet printer nozzle plates, the system of this invention could be used to inspect other relatively flat specular parts. By relatively flat, the parts should have a peak to peak variation in flatness less than the depth of field of the imaging system. The parts should be specular enough to reflect light adequate for imaging.

Although specific features of the invention are shown in some drawings and not in others, this is for convenience only as each feature may be combined with any or all of the other features in accordance with the invention.

Other embodiments will occur to those skilled in the art and are within the following claims:

What is claimed is:

1. A non-contact vision based inspection system for flat specular parts, the system comprising:
   an imaging camera defining an image and configured for taking an image of a part;
   a staging apparatus for moving the part relative to the imaging camera until an image of the part is obtained; and
   a subsystem for automatically ensuring that the image plane remains parallel to an object plane defined by the part as the part moves relative to the imaging camera while the image of the part is obtained.

2. The system of claim 1 in which the imaging camera is a linescan camera.

3. The system of claim 2 in which the part is located on a translatable table and the imaging camera is fixed in place with respect to the movement of the part and the translation table.

4. The system of claim 3 in which the subsystem for automatically ensuring includes a goniometer between the part and the translation table for rotating the orientation of the part relative to the image plane.

5. The system of claim 1 in which the subsystem for automatically ensuring that the image plane remains parallel to an object plane includes an optical source and a detector for measuring distances between each of two points on the part relative to the image plane, a goniometer on the staging apparatus, and a controller responsive to the optical source, the detector, and the goniometer for adjusting the orientation of the part and of the object plane until the object plane is parallel to the image plane.

6. The system of claim 1 further including a subsystem for automatically adjusting the distance between the image plane relative to the object plane for focusing the imaging camera.

7. The system of claim 1 further including a magazine disposed on the staging apparatus for holding a plurality of long narrow parts to be inspected in sequence.

8. the system of claim 7 which the long narrow parts are ink jet printer nozzle plates.

9. A non-contact vision based inspection system for flat specular parts including ink jet nozzle plates, the system comprising:
   a linescan camera defining an imaging plane and aimed at a part to be inspected for taking a single image of the part;
   a staging apparatus for moving the part relative to the camera until the single image of the part is obtained;
   an optical source and a detector for measuring the distance between two points on the part and the image plane;
   a goniometer between the part and the staging apparatus; and
   a controller programmed to activate the goniometer in response to the optical source and the detector until the object plane defined by the part is parallel to the image plane.

10. The system of claim 9 further including means for adjusting the height of the linescan camera above the part to focus the linescan camera.

11. The system of claim 9 further including a CCD array camera aimed at the part for locating a terminal end of the part.

12. The system of claim 11 in which the controller is further programmed to activate the staging apparatus to move a terminal end of the part proximate the optical source, to activate the optical source and then again to activate the staging apparatus to move an opposite terminal end of the part proximate the optical source, and to again activate the optical source.

13. A method of inspecting flat specular parts, the method comprising:
   placing a part defining an object plane in a spaced relationship with respect to an imaging camera defining an image plane;
   automatically adjusting one of the object plane and the image plane until they are parallel to each other; and
   moving the imaging camera in a direction parallel to the object plane until a single image of the part is recorded.

14. A method of inspecting flat specular parts including ink jet nozzle plates, the method comprising:
   locating an edge of the part;
   determining a location of an opposite edge of the part;
   calculating a height difference between each of the two edges of the part relative to an image plane defined by a position of a linescan camera;

automatically adjusting the orientation of the part until the height difference between each of the two edges of the part is below a predetermined threshold;

focusing the linescan camera at one edge of the part;

scanning the part with the linescan camera by moving the linescan camera in a direction along the image plane until the full part is imaged with the single image; and using the image of the part as input to an inspection algorithm to inspect the part for defects.

15. An imaging head for a non-contact vision based inspection system, the imaging head comprising:

an optical housing including a mount for a linescan camera and a 2D CCD array camera;

a light source;

means for directing light from the light source to a part to be inspected;

means for directing light reflected from the part simultaneously to both the linescan camera and the 2D CCD array camera; and a distance measuring device attached to the housing and configured for measuring the orientation of an image plane as defined by the linescan camera relative to an object plane as defined by the part and configured to inter-operate with a subsystem for automatically adjusting the orientation of the image plane relative to the object plane.

16. The imaging head of claim 15 in which the means for directing light reflected from the part includes a beam splitter in the optical housing positioned to direct light to both the linescan CCD camera and 2D CCD array camera.

* * * * *